US008226598B2

(12) United States Patent
Dunn et al.

(10) Patent No.: US 8,226,598 B2
(45) Date of Patent: Jul. 24, 2012

(54) COUPLING SYRINGE SYSTEM AND METHODS FOR OBTAINING A MIXED COMPOSITION

(75) Inventors: Richard L. Dunn, Fort Collins, CO (US); Cody L. Yarborough, Fort Collins, CO (US)

(73) Assignee: Tolmar Therapeutics, Inc., Fort Collins, CO (US)

( * ) Notice: Subject to any disclaimer, the term of this patent is extended or adjusted under 35 U.S.C. 154(b) by 128 days.

(21) Appl. No.: 10/634,656

(22) Filed: Aug. 5, 2003

(65) Prior Publication Data

US 2004/0127846 A1 Jul. 1, 2004

Related U.S. Application Data

(63) Continuation-in-part of application No. 09/405,463, filed on Sep. 24, 1999, now abandoned.

(51) Int. Cl.
*A61M 37/00* (2006.01)
(52) U.S. Cl. ........................................................ 604/82
(58) Field of Classification Search .............. 604/82–85, 604/110, 181–183, 186–188, 191, 218, 239–243, 604/534–535, 411, 905; 285/330, 360, 376, 285/401, 402
See application file for complete search history.

(56) References Cited

U.S. PATENT DOCUMENTS

| 2,155,658 | A |   | 4/1939  | Hermann et al. |       |
|-----------|---|---|---------|----------------|-------|
| 2,353,986 | A |   | 7/1944  | Barr ........................ | 34/5 |
| 2,477,598 | A | * | 8/1949  | Hain ............................ | 366/334 |
| 2,549,417 | A |   | 4/1951  | Brown .......................... | 604/90 |
| 3,068,188 | A |   | 12/1962 | Beste et al.    |       |
| 3,218,283 | A |   | 11/1965 | Miller et al.   |       |
| 3,219,527 | A |   | 11/1965 | Gurney         |       |
| 3,328,246 | A |   | 6/1967  | Gottfried et al. |      |
| 3,454,178 | A |   | 7/1969  | Bender et al. .............. | 215/37 |
| 3,458,622 | A |   | 7/1969  | Hill           |       |
| 3,463,158 | A |   | 8/1969  | Schmitt et al. |       |
| 3,477,431 | A |   | 11/1969 | Walecka ........................ | 604/89 |
| 3,520,949 | A |   | 7/1970  | Shepard et al. .............. | 260/857 |
| 3,696,811 | A |   | 10/1972 | Chen et al.   |       |
| 3,700,215 | A |   | 10/1972 | Hardman et al. |      |
| 3,755,558 | A |   | 8/1973  | Scribner et al. |      |
| 3,760,034 | A |   | 9/1973  | Critchfield et al. |   |
| 3,767,784 | A |   | 10/1973 | Gluck ............................ | 424/28 |
| 3,887,699 | A |   | 6/1975  | Yolles         |       |

(Continued)

FOREIGN PATENT DOCUMENTS

CA 1261549 9/1989

(Continued)

OTHER PUBLICATIONS

"International Search Report from corresponding PCT Application No. PCT/US04/25290", (Nov. 16, 2004),3 Pages.

(Continued)

*Primary Examiner* — Kevin C Sirmons
*Assistant Examiner* — Andrew Gilbert
(74) *Attorney, Agent, or Firm* — Schwegman, Lundberg & Woessner, P.A.

(57) ABSTRACT

The present invention relates generally to medical devices for mixing, preparing and administering therapeutic compositions, and more particularly to a system comprising two syringes and a locking ring wherein two compositions are mixed between the two syringes immediately prior to administration.

23 Claims, 4 Drawing Sheets

U.S. PATENT DOCUMENTS

| | | |
|---|---|---|
| 3,919,773 A | 11/1975 | Freeman |
| 3,931,678 A | 1/1976 | O'Sullivan et al. |
| 3,935,308 A | 1/1976 | Wise et al. |
| 3,939,111 A | 2/1976 | Schollenberger et al. |
| 3,949,073 A | 4/1976 | Daniels et al. |
| 3,975,350 A | 8/1976 | Hudgin et al. |
| 3,989,044 A | 11/1976 | Meierhoefer |
| 4,030,498 A | 6/1977 | Tompkins ............. 128/218 P |
| 4,040,421 A | 8/1977 | Young ................. 128/218 N |
| 4,046,145 A * | 9/1977 | Choksi et al. ............ 604/407 |
| 4,088,798 A | 5/1978 | Michaelis |
| 4,127,127 A | 11/1978 | Wong et al. |
| 4,148,871 A | 4/1979 | Pitt et al. |
| 4,161,948 A | 7/1979 | Bichon |
| 4,172,457 A | 10/1979 | Choksi et al. |
| 4,188,949 A | 2/1980 | Antoshkiw ............ 128/218 M |
| 4,240,426 A | 12/1980 | Akhavi ................. 128/218 N |
| 4,286,389 A | 9/1981 | Ogle ................................ 34/5 |
| 4,294,753 A | 10/1981 | Urist |
| 4,408,023 A | 10/1983 | Gould et al. |
| 4,439,420 A | 3/1984 | Mattei et al. |
| 4,443,430 A | 4/1984 | Mattei et al. |
| 4,447,562 A | 5/1984 | Ivani |
| 4,450,150 A | 5/1984 | Sidman ...................... 424/1.1 |
| 4,451,452 A | 5/1984 | Deibig et al. |
| 4,452,473 A | 6/1984 | Ruschke ...................... 285/81 |
| 4,455,256 A | 6/1984 | Urist |
| 4,491,479 A | 1/1985 | Lauchenauer |
| 4,501,719 A | 2/1985 | Williams ..................... 422/102 |
| 4,506,681 A | 3/1985 | Mundell ................... 128/92 D |
| 4,526,909 A | 7/1985 | Urist et al. |
| 4,526,938 A | 7/1985 | Churchill et al. |
| 4,563,489 A | 1/1986 | Urist |
| 4,568,536 A | 2/1986 | Kronenthal et al. |
| 4,570,629 A | 2/1986 | Widra |
| 4,582,640 A | 4/1986 | Smestad et al. |
| 4,595,713 A | 6/1986 | St. John |
| 4,596,574 A | 6/1986 | Urist |
| 4,614,787 A | 9/1986 | Szycher et al. |
| 4,619,989 A | 10/1986 | Urist |
| 4,629,455 A * | 12/1986 | Kanno ......................... 604/241 |
| 4,631,055 A | 12/1986 | Redl et al. ..................... 604/82 |
| 4,631,188 A | 12/1986 | Stoy et al. |
| 4,650,665 A | 3/1987 | Kronenthal et al. |
| 4,663,077 A | 5/1987 | Rei et al. |
| 4,673,396 A | 6/1987 | Urbaniak ..................... 604/211 |
| 4,677,139 A | 6/1987 | Feinmann et al. |
| 4,702,917 A | 10/1987 | Schindler .................... 424/422 |
| 4,715,369 A | 12/1987 | Suzuki et al. |
| 4,729,208 A | 3/1988 | Galy et al. ..................... 53/432 |
| 4,743,229 A * | 5/1988 | Chu ................................ 604/82 |
| 4,745,160 A | 5/1988 | Churchill et al. |
| 4,758,230 A | 7/1988 | Rycroft ....................... 604/118 |
| 4,761,471 A | 8/1988 | Urist |
| 4,766,908 A | 8/1988 | Clement ...................... 128/765 |
| 4,767,627 A | 8/1988 | Caldwell et al. |
| 4,767,861 A | 8/1988 | Boulware |
| 4,772,470 A | 9/1988 | Inoue et al. |
| 4,774,227 A | 9/1988 | Piez et al. |
| 4,780,320 A | 10/1988 | Baker |
| 4,789,732 A | 12/1988 | Urist |
| 4,793,336 A | 12/1988 | Wang |
| 4,795,804 A | 1/1989 | Urist |
| 4,800,219 A | 1/1989 | Murdoch et al. |
| 4,804,691 A | 2/1989 | English et al. ............... 523/118 |
| 4,857,456 A | 8/1989 | Urist |
| 4,857,602 A | 8/1989 | Casey et al. |
| 4,863,472 A | 9/1989 | Tormala et al. ............... 623/16 |
| 4,892,733 A | 1/1990 | Bichon et al. |
| 4,894,373 A | 1/1990 | Young |
| 4,902,296 A | 2/1990 | Bolander et al. |
| 4,904,478 A | 2/1990 | Walsdorf et al. |
| 4,905,680 A | 3/1990 | Tunc |
| 4,911,931 A | 3/1990 | Baylink |
| 4,912,141 A | 3/1990 | Kronman |
| 4,916,241 A | 4/1990 | Hayward et al. |
| 4,919,939 A | 4/1990 | Baker |
| 4,920,203 A | 4/1990 | Tang et al. |
| 4,921,697 A | 5/1990 | Peterlik et al. |
| 4,932,973 A | 6/1990 | Gendler |
| 4,933,182 A | 6/1990 | Higashi et al. |
| 4,938,763 A | 7/1990 | Dunn et al. ................. 604/891.1 |
| 4,939,131 A | 7/1990 | Benedict et al. |
| 4,942,157 A | 7/1990 | Gall et al. |
| 4,946,870 A | 8/1990 | Partain, III. et al. |
| 4,961,707 A | 10/1990 | Magnusson et al. |
| 4,978,336 A | 12/1990 | Capozzi et al. ................. 604/82 |
| 4,981,696 A | 1/1991 | Loomis et al. |
| 4,983,689 A | 1/1991 | Yu |
| 4,994,029 A | 2/1991 | Rohrbough ..................... 604/88 |
| 5,007,940 A | 4/1991 | Berg |
| 5,013,553 A | 5/1991 | Southard et al. |
| 5,047,021 A | 9/1991 | Utterberg |
| 5,077,049 A | 12/1991 | Dunn et al. .................... 424/426 |
| 5,116,315 A | 5/1992 | Capozzi et al. ................. 604/82 |
| 5,149,052 A | 9/1992 | Stoy et al. ..................... 249/105 |
| 5,234,529 A | 8/1993 | Johnson ....................... 156/345 |
| 5,250,584 A | 10/1993 | Ikada et al. |
| 5,278,201 A | 1/1994 | Dunn et al. .................... 523/113 |
| 5,278,202 A | 1/1994 | Dunn et al. .................... 523/113 |
| 5,286,763 A | 2/1994 | Gerhart et al. |
| 5,324,519 A | 6/1994 | Dunn et al. .................... 424/426 |
| 5,324,520 A | 6/1994 | Dunn et al. |
| 5,340,849 A | 8/1994 | Dunn et al. |
| 5,368,859 A | 11/1994 | Dunn et al. |
| 5,425,580 A * | 6/1995 | Beller ............................ 366/131 |
| 5,487,897 A | 1/1996 | Polson et al. .................. 424/426 |
| 5,489,266 A | 2/1996 | Grimard .......................... 604/89 |
| 5,556,279 A | 9/1996 | Wolf et al. ....................... 433/82 |
| 5,566,729 A | 10/1996 | Grabenkort et al. |
| 5,599,552 A | 2/1997 | Dunn et al. .................... 424/423 |
| 5,616,133 A * | 4/1997 | Cardenas ....................... 604/187 |
| 5,637,100 A | 6/1997 | Sudo .............................. 604/238 |
| 5,660,849 A | 8/1997 | Polson et al. ................. 424/426 |
| 5,697,918 A * | 12/1997 | Fischer et al. ................ 604/227 |
| 5,701,717 A * | 12/1997 | Gutknecht ...................... 53/117 |
| 5,702,716 A | 12/1997 | Dunn et al. .................... 424/422 |
| 5,702,717 A * | 12/1997 | Cha et al. ...................... 424/425 |
| 5,779,668 A | 7/1998 | Grabenkort ...................... 604/89 |
| 5,788,670 A | 8/1998 | Reinhard et al. ................ 604/89 |
| 5,893,842 A | 4/1999 | Imbert ............................ 604/110 |
| 5,908,054 A * | 6/1999 | Safabash et al. ................ 141/26 |
| 5,928,215 A | 7/1999 | Caizza et al. ................... 604/411 |
| 5,947,933 A | 9/1999 | Reichenbach et al. ........ 604/198 |
| 5,951,160 A | 9/1999 | Ronk ............................. 366/130 |
| 5,957,166 A * | 9/1999 | Safabash ......................... 141/26 |
| 5,984,373 A * | 11/1999 | Fitoussi et al. .................. 285/92 |
| 6,071,530 A | 6/2000 | Polson et al. .................. 424/426 |
| 6,090,092 A | 7/2000 | Fowles et al. ................. 604/413 |
| 6,106,502 A | 8/2000 | Richmond .................... 604/246 |
| 6,106,783 A | 8/2000 | Gamble ......................... 422/102 |
| 6,136,273 A | 10/2000 | Seguin et al. ................... 422/99 |
| 6,139,530 A | 10/2000 | Hiejima et al. ............... 604/140 |
| 6,143,276 A | 11/2000 | Unger ............................ 424/9.3 |
| 6,174,304 B1 | 1/2001 | Weston |
| 6,197,194 B1 | 3/2001 | Whitmore |
| 6,223,786 B1 * | 5/2001 | Castellano ....................... 604/68 |
| 6,234,196 B1 * | 5/2001 | Fischer et al. ............. 137/493.8 |
| 6,241,949 B1 | 6/2001 | Kane ............................. 422/102 |
| 6,290,680 B1 | 9/2001 | Forsberg et al. .............. 604/232 |
| 6,302,160 B2 | 10/2001 | Castellano |
| 6,364,865 B1 | 4/2002 | Lavi .............................. 604/411 |
| 6,402,207 B1 * | 6/2002 | Segal et al. .................... 285/330 |
| 6,612,624 B1 * | 9/2003 | Segal et al. .................... 285/330 |
| 2001/0016703 A1 * | 8/2001 | Wironen et al. ................. 604/89 |
| 2001/0042317 A1 | 11/2001 | Yarborough et al. ........... 34/287 |
| 2002/0055708 A1 | 5/2002 | Peterson |
| 2002/0072703 A1 * | 6/2002 | Nollert et al. .................... 604/82 |
| 2002/0101785 A1 | 8/2002 | Edwards et al. |

FOREIGN PATENT DOCUMENTS

| | | |
|---|---|---|
| CA | 2254361 | 5/1999 |
| DE | 2917037 | 4/1980 |
| DE | 3311525 | 10/1984 |
| DE | 19702564 | 9/1998 |
| DE | 19751226 | 1/1999 |
| EP | 0140766 | 5/1985 |

| | | |
|---|---|---|
| EP | 0169016 | 7/1985 |
| EP | 0171173 | 7/1985 |
| EP | 0241178 | 3/1987 |
| EP | 0242956 | 10/1987 |
| EP | 0271831 | 6/1988 |
| EP | 0297535 | 1/1989 |
| EP | 0430474 | 6/1991 |
| EP | 0560014 | 1/1993 |
| EP | 0537559 | 4/1993 |
| EP | 0539751 | 5/1993 |
| EP | 0649662 | 8/1994 |
| EP | 0743072 | 11/1996 |
| EP | 0244118 | 4/1998 |
| FR | 1109316 | 1/1956 |
| FR | 2635685 | 3/1990 |
| GB | 2197658 | 5/1988 |
| GB | 2223027 | 3/1990 |
| JP | 5-504941 | 7/1993 |
| JP | 6-196132 | 7/1994 |
| NZ | 226514 | 2/1990 |
| WO | WO-85/00969 | 3/1985 |
| WO | WO-85/02092 | 5/1985 |
| WO | WO-85/03445 | 8/1985 |
| WO | WO-89/01006 | 2/1989 |
| WO | WO-91/01126 | 7/1989 |
| WO | WO-90/00067 | 1/1990 |
| WO | WO-90/07308 | 7/1990 |
| WO | WO-97/11155 | 3/1997 |
| WO | WO-99/62578 A2 | 12/1999 |

OTHER PUBLICATIONS

"Encyclopedia of Polymer Science and Engineering", *John Wiley & Sons*, Inc., vol. 2, (1985), 236-237.

"Lyophilization", *McGraw-Hill Concise Encyclopedia of Science & Technology, Fourth Edition*, Sybil P. Parker, Editor in Chief, (1998), p. 1128.

Billmeyer, *Textbook of Polymer Science*, 3rd. Ed., (1984), 390-391.

Gilding, D. K., "Biodegradable Polymers [for implant]", *Biocompat. Clin. Implant Mater*, (1981), 209-232.

Holland, Simon J., et al., "Polymers-for Biodegradable Medical Devices, 1, The Potential of Polyesters and Controlled Macromolecular Release Systems", *Journal of Controlled Release*, 4, (1986), 155-180.

Juni, Kazukiko, et al., "Control of Release Rate of Bleomycin from Polyactic Acid Microspheres by Additives", *Chemical & Pharmaceutical Bulletin*, 33(4), (1985), 1609-1614.

Magnusson, I., et al., "New Attachment Formation Following Controlled Tissue Regeneration Using Biodegradable Membranes", *J. Periodontology*, 59, (1988), 1-6.

Salonen, J. I., et al., "Migration of Epithelial Cells on Materials Used in Guided Tissue Regeneration", *J. Periodont. Res.* 25, (1990), 215-221.

"U.S. Appl. No. 09/405,463 Advisory Action mailed May 7, 2003", 3 pgs.

"U.S. Appl. No. 09/405,463 Advisory Action mailed Dec. 11, 2001", 2 pgs.

"U.S. Appl. No. 09/405,463 Final office action mailed Sep. 18, 2001", 5 pgs.

"U.S. Appl. No. 09/405,463 Final office action mailed Oct. 7, 2002", 9 pgs.

"U.S. Appl. No. 09/405,463 Non Final office action mailed Feb. 22, 2002", 6 pgs.

"U.S. Appl. No. 09/405,463 Non Final office action mailed May 25, 2001", 8 pgs.

"U.S. Appl. No. 09/405,463 Response filed Apr. 7, 2003 to Final office action mailed Oct. 7, 2002", 10 pgs.

"U.S. Appl. No. 09/405,463 Response filed Jun. 24, 2002 to Non Final office action mailed Feb. 22, 2002", 10 pgs.

"U.S. Appl. No. 09/405,463, Response filed Nov. 14, 2001 to Final Office Action mailed Sep. 18, 2001", 5 pgs.

"U.S. Appl. No. 09/405,463, Response filed May 2, 2001 to Restriction Requirement mailed Mar. 27, 2001", 1 pg.

"U.S. Appl. No. 09/405,463, Restriction Requirement mailed Mar. 27, 2001", 4 pgs.

"U.S. Appl. No. 09/405,463 Response filed Jul. 3, 2001 to Non Final office action mailed May 25, 2001", 4 pgs.

"European Patent Application No. 04780178.2, Communication mailed Nov. 14, 2007", 4 pgs.

"European Patent Application No. 04780178.2, Supplementary European Search Report mailed Aug. 9, 2007", 2 pgs.

"PCT Application No. PCT/US2004/025290, International Preliminary Report on Patentability mailed Feb. 16, 2006", 5 pgs.

"Australian Application Serial No. 2004264341, Examiner's First Report mailed on Jun. 15, 2009", 2 pgs.

"Australian Application Serial No. 2004264341, Second Examiner Report mailed Aug. 4, 2010", 2 pgs.

"Canadian Application Serial No. 2,534,671, Office Action mailed Aug. 26, 2010", 2 Pgs.

"European Application Serial No. 04780178.2, Office Action Mailed Sep. 9, 2010", 4 pgs.

"European Application Serial No: 2004264341, Office Action Response filed Jul. 6, 2010", 13 pgs.

"European Patent Application No. 04780178.2, Reply filed Mar. 14, 2008 to Communication mailed Nov. 14, 2007", 11 pgs.

"Japanese Application Serial No. 2006-522717, Office Action mailed Feb. 16, 2010", 4 pgs.

"Japanese Patent Application Serial No. 2006-522717, Office Action mailed Feb. 16, 2010", (w/ English Translation), 4 pgs.

"Japanese Patent Application Serial No. 2006-522717, Response filed Aug. 13, 2010 to First Office Action mailed Feb. 16, 2010", (w/ English Translation of Claims), 10 pgs.

"U.S. Appl. No. 10/456,814 Non Final Office Action mailed Jul. 22, 2011", 13 pgs.

"U.S. Appl. No. 10/456,814 Response filed Nov. 22, 2011 to Non Final Office Action mailed Jul. 22, 2011", 20 pgs.

"U.S. Appl. No. 10/456,814, Response filed Mar. 7, 2008 to Decision on Pre-Appeal Brief Request mailed Feb. 7, 2008", 15 pgs.

"U.S. Appl. No. 10/456,814, Advisory Action mailed Apr. 14, 2005", 3 pgs.

"U.S. Appl. No. 10/456,814, Advisory Action mailed Jun. 4, 2007", 3 pgs.

"U.S. Appl. No. 10/456,814, Advisory Action mailed Jun. 15, 2006", 3 pgs.

"U.S. Appl. No. 10/456,814, Examiner Interview Summary mailed Jun. 27, 2005", 3 pgs.

"U.S. Appl. No. 10/456,814, Examiner Interview Summary mailed Sep. 14, 2005", 1 pg.

"U.S. Appl. No. 10/456,814, Examiner Interview Summary mailed Nov. 10, 2011", 3 pgs.

"U.S. Appl. No. 10/456,814, Final Office Action mailed Mar. 1, 2007", 5 pgs.

"U.S. Appl. No. 10/456,814, Final Office Action mailed Mar. 22, 2006", 8 pgs.

"U.S. Appl. No. 10/456,814, Final Office Action mailed Jun. 18, 2009", 7 pgs.

"U.S. Appl. No. 10/456,814, Final Office Action mailed Dec. 28, 2004", 6 pgs.

"U.S. Appl. No. 10/456,814, Non Final Office Action mailed Feb. 18, 2004", 5 pgs.

"U.S. Appl. No. 10/456,814, Non Final Office Action mailed Aug. 30, 2006", 5 pgs.

"U.S. Appl. No. 10/456,814, Non Final Office Action mailed Sep. 22, 2005", 5 pgs.

"U.S. Appl. No. 10/456,814, Non Final Office Action mailed Dec. 29, 2010", 7 pgs.

"U.S. Appl. No. 10/456,814, Non-Final Office Action mailed Jan. 7, 2009", 6 pgs.

"U.S. Appl. No. 10/456,814, Non-Final Office Action mailed May 29, 2008", 9 pgs.

"U.S. Appl. No. 10/456,814, Pre-Appeal Brief Request filed Jul. 5, 2007", 5 pgs.

"U.S. Appl. No. 10/456,814, Preliminary Amendment mailed Jun. 6, 2003", 3 pgs.

"U.S. Appl. No. 10/456,814, Response filed Mar. 22, 2005 to Final Office Action mailed Dec. 28, 2004", 14 pgs.

"U.S. Appl. No. 10/456,814, Response filed Apr. 7, 2009 to Non Final Office Action mailed Jan. 7, 2009", 17 pgs.

"U.S. Appl. No. 10/456,814, Response filed Apr. 29, 2011 to Non Final Office Action mailed Dec. 29, 2010", 15 pgs.

"U.S. Appl. No. 10/456,814, Response filed May 1, 2007 to Final Office Action mailed Mar. 1, 2007", 12 pgs.

"U.S. Appl. No. 10/456,814, Response filed May 17, 2004 to Non Final Office Action mailed Feb. 18, 2004", 9 pgs.

"U.S. Appl. No. 10/456,814, Response filed May 22, 2006 to Final Office Action mailed Mar. 22, 2006", 15 pgs.

"U.S. Appl. No. 10/456,814, Response filed Sep. 25, 2008 to Non-Final Office Action mailed May 29, 2008", 13 pgs.

"U.S. Appl. No. 10/456,814, Response filed Nov. 30, 2006 to Non Final Office Action mailed Aug. 30, 2006", 12 pgs.

"U.S. Appl. No. 10/456,814, Response filed Dec. 16, 2009 to Final Office Action mailed Jun. 18, 2009", 15 pgs.

"U.S. Appl. No. 10/456,814, Response filed Dec. 22, 2005 to Non Final Office Action mailed Aug. 22, 20 05", 12 pgs.

"Japanese Application Serial No. 2006-522717, Examiner Decision of Final Refusal mailed Sep. 22, 2011", 1 pg.

"U.S. Appl. No. 10/456,814, Final Office Action mailed Mar. 29, 2012", 20 pgs.

US 4,450,140, 05/1984, Sidman (withdrawn)

* cited by examiner

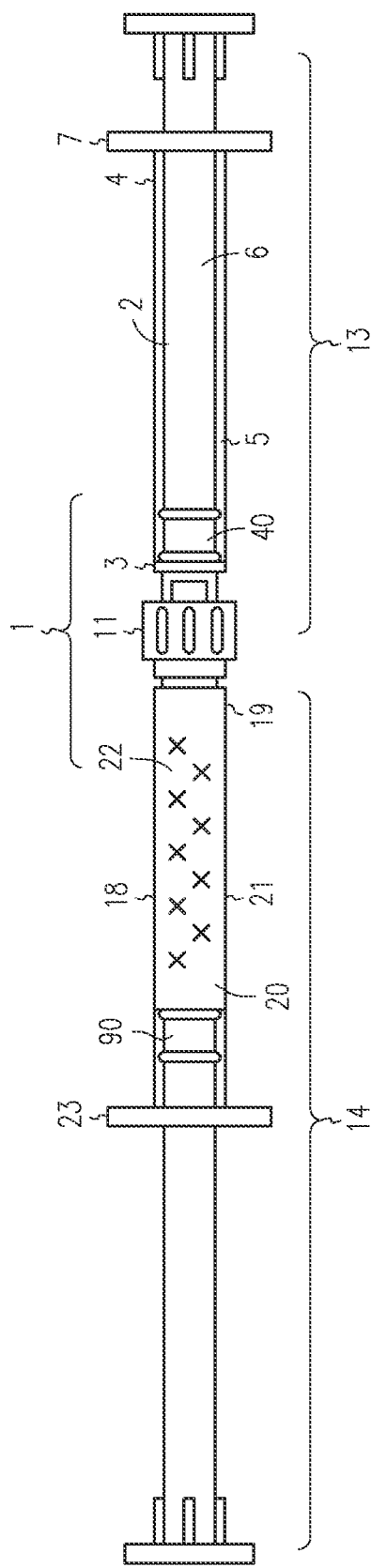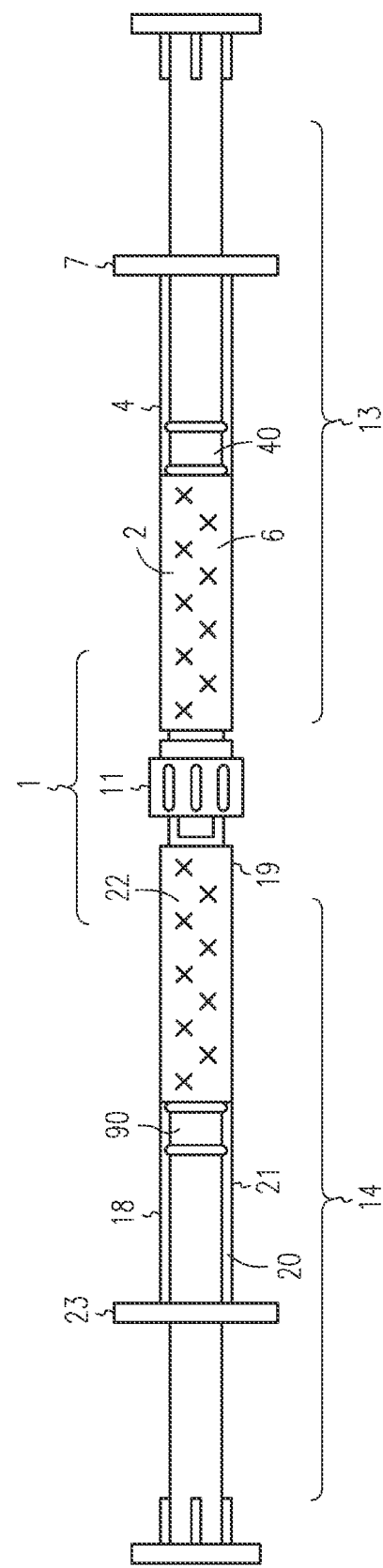

COUPLING SYRINGE SYSTEM AND METHODS FOR OBTAINING A MIXED COMPOSITION

RELATED APPLICATIONS

This application is a continuation-in-part of U.S. patent application Ser. No. 09/405,463, filed Sep. 24, 1999, now abandoned, which application is incorporated herein by reference.

BACKGROUND OF THE INVENTION

A large number of drugs and other medicaments are routinely prepared and administered to patients in a health care facility. Sometimes, two components of a therapeutic composition are required to be mixed immediately prior to administration. One method for mixing therapeutic compositions immediately prior to administration includes mixing two solutions in a mixing vessel, whereupon the mixture is drawn into a syringe, and the resulting mixed composition is then applied to an appropriate site of the patient. However, this process is often cumbersome, a significant amount of the drug may be lost, and the time between the mixing and the application is often too long with sensitive compositions (i.e., compositions that, upon mixing, must be immediately administered).

Another method for mixing therapeutic compositions immediately prior to administration employs two syringes that are clamped together. Output ends of the syringes are inserted into a Y-shaped coupling device having two input openings and a single output opening. Mixing occurs in the Y-shaped coupling device or in a needle connected to the single output end of the Y-shaped coupling device. However, with this type of arrangement, control over the degree of mixing does not exist and the degree of mixing, therefore, may be inadequate.

Another method for mixing therapeutic compositions immediately prior to administration includes coupling two syringes with an independent coupling means, thereby allowing the contents of one syringe to be mixed with the contents of the other coupled syringe. The independent coupling means, however, provides a space where there is very little agitation due to plug flow of the contents. The contents, therefore, do not mix well. Additionally, when the syringes are uncoupled (i.e., disengaged), the contents have to be aspirated out of the independent coupling means or they will be lost. In addition, the independent coupling means must be removed and discarded before attaching a needle to the delivery or injection syringe.

U.S. Pat. No. 4,994,029 (the '029 patent) discloses a syringe mixer and injector device formed of an injector and an adapter having opposed interconnectable nozzles on their facing ends and sockets and a short tubular spike in each socket to penetrate the stopper of a vial when connected to that socket. See, the '029 patent col. 2, ll. 24-31. It is among the additional objects of the invention to provide such a device which can be used with a receiving vial charged with a medicament solid or liquid, and a charging vial charged with a medicament liquid for one-way transfer to the receiving vial for admixing the medicaments therein without retransfer to the charging vial. Id. at col. 2, ll. 38-24 and col. 6, ll. 23-30. The injector inner end has a connection, provided with a nozzle recess containing a tapered, e.g. central, spout defining the inner terminus of pathway 5 and a lock connection formation, such as a luer lock tab, arranged to form a male connection formation for interconnecting releasably with mating parts on adapter 30. Col. 4, ll. 5-12. Since the '029 patent explicitly discloses that the system is made for one-way transfer, without recharging the charging vial, it would not be suitable for the recombination of materials between two syringes.

Since the system disclosed in the '029 patent was not contemplated for multiple-pass use (i.e., recombination of materials between two syringes), the skilled artisan would not use the '029 patent disclosure for a syringe system wherein multiple-pass use is desired. This is so because a system not contemplated for multiple-pass use, that is nonetheless employed for multiple-pass use, can result in an appreciable amount of sample loss (e.g., leakage). This is especially troublesome when the drug is expensive (e.g. leuprolide acetate). This is also troublesome since the U.S. Food and Drug Administration (FDA) requires that the health care professionals administer an active ingredient in a precise and known amount. Obviously, this requirement cannot be met when there is an appreciable amount of sample loss due to the syringe assembly.

U.S. Pat. No. 6,223,786 (the '786 patent) is directed to devices and methods for mixing medication and filling an ampule of a needle-less injector prior to an injection, which includes a reagent holder and a diluent holder. See, the '786 patent, col. 2, ll. 6-15. The diluent holder includes a plunger which is depressed to load the diluent from the diluent holder into the reagent holder to mix with the reagent to produce a liquid medication for filling the ampule of the needle-less injector. Id. at col. 2, ll. 20-25. In further embodiments, the reagent holder further includes a reagent plunger rod. Id. at col. 2, ll. 24-26. There is no disclosure or suggestion either explicitly or implicitly to include a male or female end forming a fluid tight engagement. In fact, the only engagement disclosed is a thread like engagement without any mention to fluid tightness. Moreover, the engagement disclosed by the '786 cannot be locked, as the threaded engagement has no means of locking.

In the most simplistic embodiment, the '786 patent discloses a four part system: diluent holder, support brushing, reagent holder, and the needleless injector; while the '029 patent discloses a four part system: injector, plunger vial, adaptor and charging vial. The presence of multiple (e.g., four) components increases the likelihood of human error when mixing and administering a drug. Additionally, the presence of multiple components increases the likelihood of an occurrence of sample loss (e.g., leakage).

Thus, there is a need for a syringe system wherein components of a composition can be easily mixed by the end user without losing a significant amount of mixed composition during the mixing process and wherein the mixed composition can be easily and rapidly administered to a patient. Such a syringe system will have a relatively few number of interconnecting parts, to minimize human error and to minimize sample loss. Additionally, the syringe system will effectively mix the contents located therein without sample loss, such that it will be approved by the FDA when used with drugs that must be administered in a known, discrete and precise amount (e.g., leuprolide acetate).

SUMMARY OF THE INVENTION

The present invention provides a syringe system wherein components of a composition can be easily mixed by the end user without losing a significant amount of mixed composition during the mixing process and wherein the mixed composition can be easily and rapidly administered to a patient. The syringe system has a relatively few number of interconnecting parts, to minimize human error and to minimize sample loss. Additionally, the syringe system effectively mixes the contents located therein without sample loss, such that it can be approved by the FDA when used with drugs that must be administered in a known, discrete and precise amount (e.g., leuprolide acetate).

The present invention provides a coupling syringe system for obtaining a mixed composition, a method for forming a mixed composition that employs such a coupling syringe system, and a method for administering a mixed composition to a patient, that employs such a coupling syringe system.

The coupling syringe system includes a first syringe, a first syringe plunger, a second syringe, and a second syringe plunger. The first syringe includes a first syringe barrel having a first syringe open proximal end and a first syringe distal end. The first syringe further includes a first syringe tip with a male end portion, wherein the male end portion has a locking ring and a tip. The first syringe barrel has a first syringe inner surface. The first syringe plunger is slidably disposed within the first syringe barrel. The first syringe plunger is in fluid-tight engagement with the first syringe inner surface. The second syringe includes a second syringe barrel having a second syringe open proximal end and a second syringe distal end. The second syringe further includes a second syringe tip with a female end portion, wherein the female end portion includes one or more exteriorly protruding members adapted to detachably fit the locking ring. The second syringe barrel has a second syringe inner surface. The second syringe plunger is slidably disposed within the second syringe barrel. The second syringe plunger is in fluid-tight engagement with the second syringe inner surface. The female end portion has an opening therein. The opening is sized and configured to receive the tip of the male end portion therein. The locking ring couples the first syringe to the second syringe when the tip of the male end portion is disposed within the female end portion, forming a fluid tight engagement.

BRIEF DESCRIPTION OF THE DRAWINGS

FIG. 1 illustrates a coupled syringe system with a mixed composition formed from introducing the composition of the syringe with the male end portion into the syringe with the female end portion.

FIG. 2 illustrates a coupled syringe system with a mixed composition formed from introducing the composition of the syringe with the female end portion into the syringe with the male end portion.

DETAILED DESCRIPTION OF THE INVENTION

The coupling syringe system of the present invention allows for the effective mixing of compositions immediately prior to administration. The mixing does not result in a significant loss of the composition. In addition, the time between the mixing and the administration of the composition is minimal, such that a sensitive composition (i.e., a composition that, upon mixing, must be immediately administered) is not chemically or physically altered (i.e., there is minimal decomposition). The use of the coupling syringe system of the invention does not result in a plug flow of the contents. In addition, the coupling syringe system can conveniently be disassembled and a needle can conveniently be attached to the syringe which includes a male end portion and a locking ring.

Figure 3:
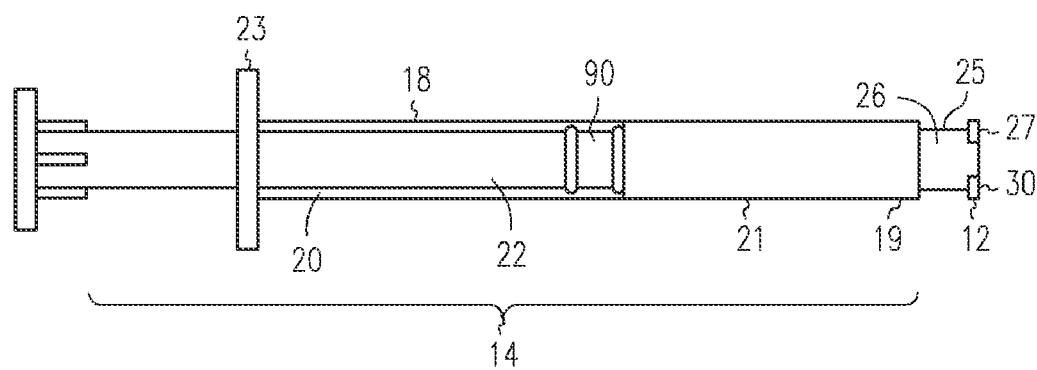
FIG. 3 illustrates a syringe with a female end portion.
Figure 4:
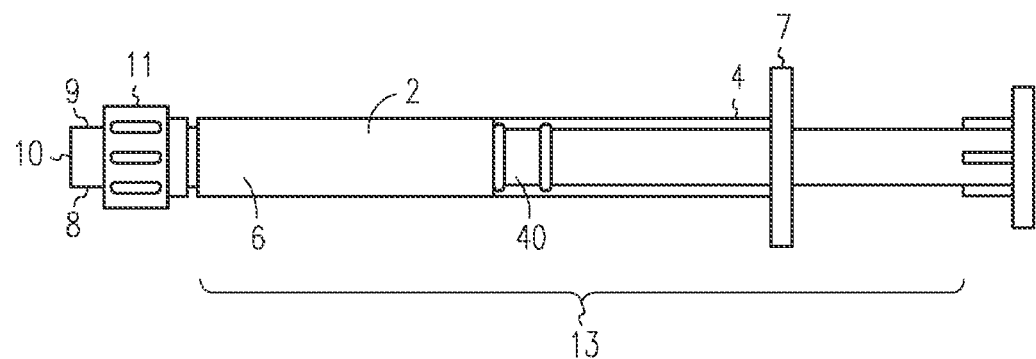
FIG. 4 illustrates a syringe with a male end portion.
Figure 5:
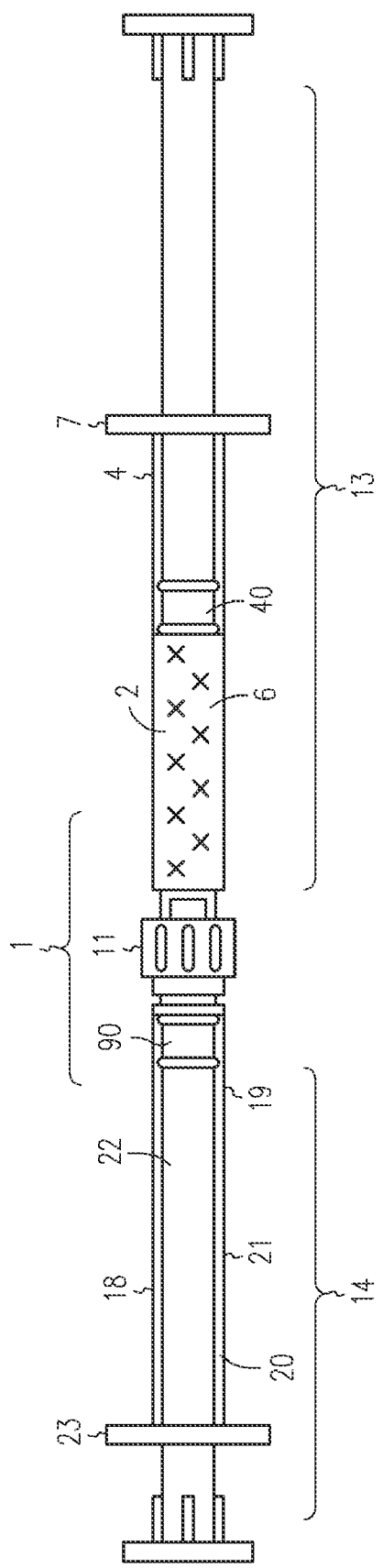
FIG. 5 illustrates a coupled syringe system with a mixed composition formed from introducing the composition of the syringe with the female end portion into the syringe with the male end portion.

Referring to FIGS. 1-6, a coupling syringe system of the present invention is identified generally by the numeral 1. As shown in FIGS. 1, 2, and 5, syringe system 1 includes a first syringe 13 and a second syringe 14. The first syringe 13 includes a barrel 2. The barrel 2 has a distal end 3, an open proximal end 4, and a generally cylindrical wall 5 extending between the ends to define a fluid receiving chamber 6. Cylindrical wall 5 of the first syringe barrel defines an outside diameter along much of its length. An outwardly projecting finger flange 7 is defined near proximal end 4 of the first syringe barrel 2 for facilitating digital manipulation of the first syringe. Additionally, as shown in FIG. 4, distal end 3 of the first syringe barrel 2 is characterized with a tip 8. Tip 8 is provided with a fluid passage 9 extending therethrough and communicating with fluid receiving chamber 6. The tip 8 is also provided with a male end portion 10 wherein the male end portion 10 is provided with a locking ring 11.

The locking ring 11 is configured such that the interior of the locking ring 11 contains threads which are adapted to receive protruding members 12 exteriorly disposed on the female end portion of the second syringe 14 as shown in FIG. 3. The locking ring 11 is designed to interlock the first syringe 13 (i.e., the syringe including the male end portion) and the second syringe 14 (i.e., the syringe including the female end portion). In addition, the locking ring 11 is configured to detachably connect to a discharge assembly 15. Specifically, the discharge assembly 15 can include a needle 16 (see FIG. 6).

As shown in FIGS. 1, 2, and 5, syringe system 1 also includes a second syringe 14 having a barrel 18. The barrel 18 has a distal end 19, an open proximal end 20, and a generally cylindrical wall 21 extending between the ends to define a fluid receiving chamber 22. Cylindrical wall 21 of the second syringe barrel defines an outside diameter along much of its length. An outwardly projecting finger flange 23 is defined near proximal end 20 of the second syringe barrel 18 for facilitating digital manipulation of the second syringe 14. As shown in FIG. 3, distal end 19 of the second syringe barrel is characterized with a tip 25. Tip 25 is provided with a fluid passage 26 extending therethrough and communicating with fluid receiving chamber 22. The tip 25 is also provided with a female end portion 27 wherein the female end portion 27 is configured to detachably connect to the locking ring 11. The female end portion 27 includes one or more (e.g., 1, 2, 3, or 4) exteriorly protruding members 30 adapted to detachably engage the locking ring 11. The protruding members 30 are configured such that they can thread into the locking ring 11.

As shown in FIGS. 1, 2, 4, and 6, a plunger 40 is disposed in fluid receiving chamber 6 and is in sliding fluid-tight engagement with cylindrical wall 5 of syringe barrel 2. Sliding movement of plunger 40 in a distal direction causes the composition (i.e., solid, liquid, or mixture thereof) in chamber 6 to be expelled through passage 9 of tip 8 (see FIG. 4) and into fluid receiving chamber 22 (see FIGS. 1, 2, 3, and 6) thereby mixing the composition (i.e., solid, liquid, or mixture thereof) of chamber 6 with the composition (i.e., solid, liquid, or mixture thereof) of chamber 22. Conversely, sliding movement of plunger 40 in a proximal direction draws the composition (i.e., solid, liquid, or mixture thereof) in chamber 22 through passage 26 and into fluid receiving chamber 6 thereby mixing the composition (i.e., solid, liquid, or mixture thereof) of chamber 26 with the composition (i.e., solid, liquid, or mixture thereof) of chamber 22. It is appreciated that those skilled in the art understand that any combination of the above steps can be carried out and repeated until such time as an effective amount of mixing is attained.

As shown in FIGS. 1, 2, 3, and 6, a plunger 90 is disposed in fluid receiving chamber 22 and is in sliding fluid-tight engagement with cylindrical wall 21 of syringe barrel 18. Sliding movement of plunger 90 in a distal direction causes the composition (i.e., solid, liquid, or mixture thereof) in chamber 22 to be expelled through passage 26 of tip 25 and into fluid receiving chamber 6 (see FIGS. 1, 2, 4, and 6) thereby mixing the composition (i.e., solid, liquid, or mixture thereof) of chamber 22 with the composition (i.e., solid, liquid, or mixture thereof) of chamber 6. Conversely, sliding movement of plunger 90 in a proximal direction draws the composition (i.e., solid, liquid, or mixture thereof) in chamber 6 through passage 9 and into fluid receiving chamber 22 thereby mixing the composition (i.e., solid, liquid, or mixture thereof) of chamber 6 with the composition (i.e., solid, liquid, or mixture thereof) of chamber 22. It is appreciated that those skilled in the art understand that any combination of the above steps can be carried out and repeated until such time as an effective amount of mixing is attained.

Figure 6:
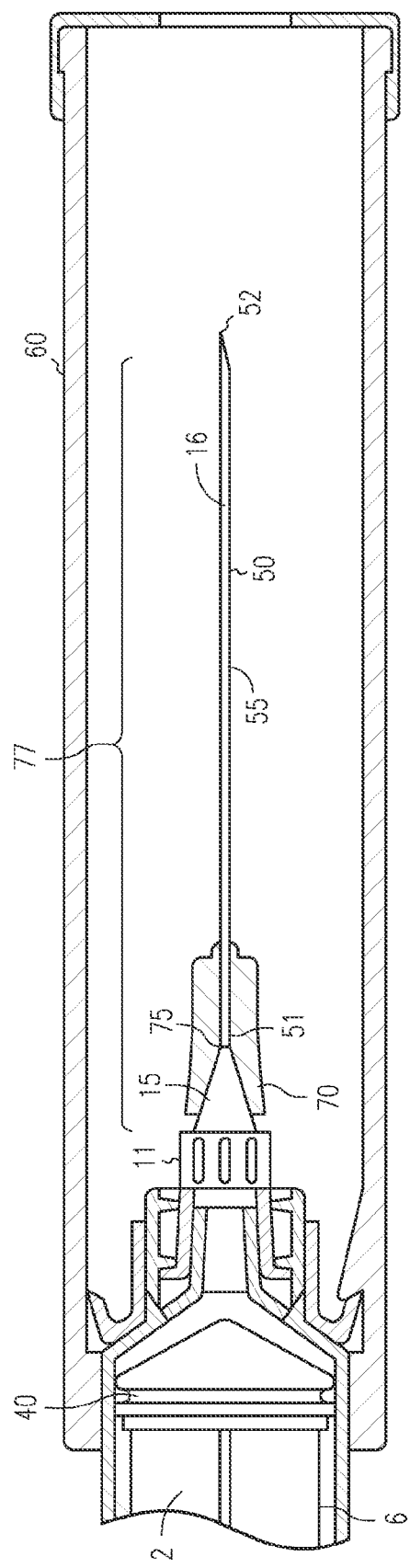
FIG. 6 illustrates a syringe with a male end portion detachably connected to a discharge assembly wherein the discharge assembly includes a needle and wherein a needle cover is removably mounted over the needle cannula.

As shown in FIG. 6, a discharge assembly 15 can be connected to the locking ring 11 of the first syringe 13. More particularly, the discharge assembly 15 includes needle cannula 50 having a proximal end 51, a sharp distal end 52 and a lumen 55 extending therebetween. A hub 75 joined to the cannula so that the lumen 55 is in fluid communication with the hub 75. Tip 8 fits into hub 75 and frictionally engages the hub 75 so that the lumen 55 of needle cannula communicates with passage through tip 8 and further communicates with fluid receiving chamber 6 of syringe barrel 2. In this embodiment, needle assembly 77 is removably mounted to tip 8. However, it is within the purview of the present invention to include a needle cannula that is directly and permanently mounted to the syringe tip.

As shown in FIG. 6, a needle cover 60 can be removably mounted over needle cannula 50 to prevent accidental sticks prior to use of syringe assembly 70. Needle cover 60 can be removed from syringe assembly 70 immediately prior to use.

In an alternative embodiment, a first securing device can conveniently be mounted on the interior surface of barrel 2 or on the inside of barrel 18. The first securing device, upon engaging with a second securing device mounted on the external surface of plunger 40 or plunger 90, respectively, can prohibit the plunger 40 or the plunger 90 from disengaging from barrel 2 or the barrel 18, respectively.

The first syringe and the second syringe can conveniently be manufactured from any suitable material. Typically, both the first syringe and the second syringe are each independently manufactured from glass or plastic (e.g., polypropylene, polyethylene, polycarbonate, polystyrene, and the like).

The size of both the first syringe and second syringe can independently be any suitable size. Suitable sizes include a syringe barrel of about 0.01 to about 100 cc, about 0.1 cc to about 50 cc, about 0.1 cc to about 25 cc, or about 0.5 cc to about 10 cc.

The first syringe 13 (i.e., the syringe including the male end portion and locking ring) can conveniently be manufactured by any suitable process. The first syringe can conveniently be manufactured by an injecting molding process where the entire syringe is made as one unit. Alternatively, the first syringe can be manufactured by independently molding the syringe and locking ring and then mounting (i.e., attaching) the locking ring and first syringe. Preferably, the locking ring is permanently attached to the first syringe. Although the ring can also be mounted coaxially and rotably with tip 8 by a flange and seal configuration. In this configuration, the ring can be rotated around the tip. Typically, the locking ring is permanently attached to the first syringe by welding the two pieces together.

The second syringe 14 (i.e., the syringe including the female end portion) can conveniently be manufactured by any suitable process. The second syringe can be manufactured by an injecting molding process where the entire syringe is made as one unit.

Each composition to be combined with a syringe can independently be a solid, liquid, or mixture thereof. In addition, the solid can be a powder or crystalline material. As used herein, a mixture of a solid and a liquid can be a heterogeneous phase (e.g., an emulsion or a colloidal suspension). Alternatively, a mixture of a solid and a liquid can be a homogeneous phase (i.e., a solid completely dissolved in a liquid).

Each composition can independently include one or more (e.g., 1, 2, or 3) compounds. In addition, the compound of the composition can be a drug delivery system, a drug (i.e., pharmaceutical) or a pharmaceutically acceptable salt thereof, a liquid carrier, a liquid, a lipid formulation, or a vaccine.

Any suitable drug delivery system can be employed. A suitable drug delivery system includes, but is not limited to, is the Atrigel® delivery system mixed with doxycycline or leuprolide acetate. The Atrigel® system is described in U.S. Pat. No. 5,278,201, the disclosure of which is incorporated herein by reference.

Any suitable drug (i.e., pharmaceutical) or pharmaceutically acceptable salt thereof can be employed. Suitable classes of drugs include antibiotics, peptides, hormones, analgesics, growth factors, and any agent described in U.S. Pat. No. 4,938,763B1, the disclosure of which is incorporated herein by reference. The drug can exist as a solid (e.g., crystal or powder), an oil, or as a liquid. In addition, the drug may exist in a microcapsule containing the drug or as a microparticle.

Any suitable liquid carrier can be employed. Suitable liquid carriers include a collagen solution, a sterile aqueous solution, a sterile saline solution, an alcoholic solution, or any suitable mixture thereof. In addition, the liquid carrier can be an emulsion formed from a mixture of an oil or lipid with a sterile aqueous solution or a sterile saline solution.

Specifically, the liquid drug delivery system can be the Atrigel® system mixed with a powder drug (e.g., doxycycline or leuprolide acetate).

Specifically, the drug can be an antibiotic or growth factor.

Specifically, the liquid carrier can be a collagen solution and a powder drug.

Specifically, the liquid carrier can be a sterile aqueous or a sterile saline solution and a powder drug.

Specifically, the liquid can be an alcohol and a drug mixed with a sterile saline or a sterile aqueous solution.

Specifically, the lipid formulation can be mixed with a sterile aqueous solution or a sterile saline solution to form an emulsion.

Specifically, the liquid carrier (e.g., a sterile aqueous solution or a sterile saline solution) can be mixed with a microcapsule or a microparticle containing drug.

Specifically, the vaccine solution can be mixed with an oil to form an emulsion.

Any suitable method of administration can be employed. Typically, the mixed composition can be administered to a patient by intravenous, intramuscular, intraperitoneal, or subcutaneous routes.

EXAMPLES

Both the amount of drug and the drug content, delivered from a syringe system of the present invention, is relatively uniform. Additionally, there is relatively low sample loss when delivering a drug from syringe system of the present invention.

Example 1

The LA-2575 30.0 mg drug product when injected subcutaneously forms a biodegradable implant that delivers 30.0 mg of leuprolide acetate (LA) over a four-month period. The drug product is composed of two separate syringes. Syringe A with a female Luer Lok fitting contains the drug delivery vehicle, and Syringe B with a male Luer Lok fitting contains lyophilized LA. To constitute the product for injection, Syringe A and Syringe B are connected, and the contents are passed back and forth until blended. After mixing, the two syringes are separated, a hypodermic needle is attached to Syringe B, and the constituted drug product is administered subcutaneously to the patient.

A fraction of the constituted drug product is trapped in the hub of Syringe A after the mixing process and in the hub and needle of Syringe B after injection. To meet the targeted delivery values, this retained drug product must be accounted for when calculating the fill weights for both syringes. Also, the amount of material and drug delivered from the mixed syringe must be consistent in quantity to meet strict FDA rules for administered drug. To determine whether the amount of material and drug administered was consistent, an experiment was performed with the following supplies:

- Syringe A, a 1.2 ml syringe (UltraTek) molded with a female Luer-Lok® fitting, contains the vehicle 75:25 Poly (D,L-lactide-co-glycolide) (PLG) dissolved in a biocompatible solvent N-methyl 2-pyrrolidone (NMP). The fill weight was 560 mg vehicle.
- Syringe B, a 1.0 mL syringe (Becton-Dickinson) molded with a male Luer-Lok® fitting, contains lyophilized LA. The fill weight was 35.8 mg of lyophilized LA.

Each of three lab analysts constituted 10 replicate units using 30 mixing cycles and determined delivered mass and % LA content. The data given in the table show that the delivered mass was consistent with a delivered mass of 504.4±6.55 mg and the mixing was uniform with a drug content of 5.6±0.19%. These data show that the syringe coupling system gives uniform mixing of the contents and reproducible delivery of the mixed mass.

|         |        | 30 Cycles         |        |
|---------|--------|-------------------|--------|
| Analyst | Sample | Del. Mass (mg)    | LA (%) |
| 1 (ST)  | 1      | 508.6             | 5.7%   |
|         | 2      | 517.3             | 5.7%   |
|         | 3      | 512.8             | 5.8%   |
|         | 4      | 514.9             | 5.7%   |
|         | 5      | 508.7             | 5.7%   |
|         | 6      | 505.9             | 5.5%   |
|         | 7      | 504.4             | 5.8%   |
|         | 8      | 506.2             | 5.7%   |
|         | 9      | 512.6             | 5.8%   |
|         | 10     | 503.6             | 5.7%   |
| 2 (SV)  | 1      | 508.8             | 5.7%   |
|         | 2      | 504.2             | 5.7%   |
|         | 3      | 511.7             | 5.6%   |
|         | 4      | 509.9             | 5.6%   |
|         | 5      | 501.0             | 5.7%   |
|         | 6      | 502.3             | 5.5%   |
|         | 7      | 500.1             | 5.6%   |
|         | 8      | 499.7             | 5.7%   |
|         | 9      | 505.1             | 5.7%   |
|         | 10     | 505.0             | 5.7%   |
| 3 (RM)  | 1      | 494.9             | 5.1%   |
|         | 2      | 499.4             | 5.4%   |
|         | 3      | 501.6             | 5.7%   |
|         | 4      | 506.0             | 5.7%   |
|         | 5      | 497.9             | 5.6%   |
|         | 6      | 505.3             | 5.7%   |
|         | 7      | 501.0             | 5.4%   |
|         | 8      | 502.8             | 5.0%   |
|         | 9      | 485.8             | 5.2%   |
|         | 10     | 494.5             | 5.6%   |
| Mean    |        | 504.4             | 5.6%   |
| SD      |        | 6.55              | 0.19%  |
| % RSD   |        | 1.3%              | 3.5%   |

Example 2

The 6-Month ELIGARD 45.0 mg drug product when injected subcutaneously forms a biodegradable implant that delivers 45.0 mg of leuprolide acetate (LA) over a six-month period. The drug product is composed of two separate syringes. Syringe A with a female Luer Lok fitting contains the drug delivery vehicle, and Syringe B with a male Luer Lok fitting contains lyophilized LA. To constitute the product for injection, Syringe A and Syringe B are connected, and the contents are passed back and forth until blended. After mixing, the two syringes are separated, a hypodermic needle is attached to Syringe B, and the constituted drug product is administered subcutaneously to the patient.

A fraction of the constituted drug product is trapped in the hub of Syringe A after the mixing process and in the hub and needle of Syringe B after injection. To meet the targeted delivery values, this retained drug product must be accounted for when calculating the fill weights for both syringes. An experiment was conducted to determine the amount of total mass delivered, the amount of drug, and the drug content when the two syringes were mixed. The following supplies were used in this experiment:

- Syringe A, a 1.2 ml syringe (UltraTek) molded with a female Luer-Lok® fitting, contains the vehicle 85:15 Poly (D,L-lactide-co-glycolide) (PLG) dissolved in a biocompatible solvent N-methyl 2-pyrrolidone (NMP). The fill weight of the polymer vehicle was 410±2 mg.
- Syringe B, a 3.0 mL syringe (Becton-Dickinson) molded with a male Luer-Lok® fitting, contains lyophilized LA. The fill weight of this syringe was 56.3 mg of LA.

Each of three lab analysts constituted six replicate units using 60 mixing cycles and determined delivered mass and % LA content. The results given in the table show that the delivered mass was consistent with 371.4±4.5 mg, the amount of drug delivered at 45.5±0.8 mg, and the drug content at 12.3±0.2%. These data show that the unique syringe coupling system gives both uniform mixing of the contents and reproducible delivery of the mixed mass.

| Analyst | Sample | 60 Cycles | | |
|---|---|---|---|---|
| | | Del. Mass (mg) | LA Rev (mg) | LA Recov (%) |
| 1 (ST) | 1 | 376.8 | 46.0 | 12.2% |
| | 2 | 376.0 | 46.3 | 12.3% |
| | 3 | 360.8 | 43.6 | 12.1% |
| | 4 | 373.2 | 45.7 | 12.2% |
| | 5 | 378.3 | 46.2 | 12.2% |
| | 6 | 372.8 | 46.9 | 12.6% |
| 2 (SK) | 1 | 376.6 | 45.2 | 12.0% |
| | 2 | 372.4 | 45.4 | 12.2% |
| | 3 | 365.1 | 44.7 | 12.2% |
| | 4 | 368.1 | 45.5 | 12.4% |
| | 5 | 373.5 | 45.8 | 12.3% |
| | 6 | 372.9 | 46.5 | 12.5% |
| 3 (MA) | 1 | 372.1 | 44.4 | 11.9% |
| | 2 | 370.4 | 44.7 | 12.1% |
| | 3 | 366.5 | 45.4 | 12.4% |
| | 4 | 367.1 | 45.5 | 12.4% |
| | 5 | 371.1 | 45.9 | 12.4% |
| | 6 | 370.6 | 45.4 | 12.3% |
| Mean | | 371.4 | 45.5 | 12.3% |
| Std. Dev | | 4.5 | 0.8 | 0.2% |
| % RSD | | 1.2% | 1.8% | 1.3% |

What is claimed:

1. A coupling syringe system comprising:
   a first syringe including a first syringe barrel having a first syringe distal end, the first syringe further including a first syringe tip with an integral male end portion, an inner surface of the male end portion forming a single fluid passage, and a locking ring at the first syringe distal end, wherein the locking ring is spaced from an outer surface of the male portion;
   a first syringe plunger slidably disposed within the first syringe barrel and configured to move to a position at the first syringe distal end, a first volume of a first composition is retained within the first syringe barrel including the first syringe tip;
   a second syringe including a second syringe barrel having a second syringe distal end, the second syringe further including at the second syringe distal end a second syringe tip with an integral female end portion coupled with the second syringe barrel and one or more exteriorly protruding members adapted to detachably fit the locking ring, wherein the female end portion has an opening defined by an opening wall, which supports the one or more exteriorly protruding members;
   a second syringe plunger slidably disposed within the second syringe barrel and configured to move to a position at the second syringe distal end, a second volume of a second composition is retained within the second syringe barrel;
   wherein the first syringe and the second syringe are each sized to contain a single dose; and
   wherein, when the first and second syringes are coupled, the male end portion is received by the opening of the female end portion at the first and second syringe distal ends, the single fluid passage of the integral male end portion extends into the female end portion between the first and second syringe barrels, and the opening wall and the one or more exteriorly protruding members are received by the spacing between the locking ring and the outer surface of the male end portion, thereby allowing for a single, fluid tight attachment site configured for back and forth transfer and mixing of the first and second volumes of the first and second compositions between the first and second syringes through the single fluid passage, wherein a mixing volume including the first and second volumes is substantially fully transitioned between the first and second syringes in corresponding first and second mixing configurations:
   in the first mixing configuration, the mixing volume is substantially fully retained within the first syringe barrel, and
   in the second mixing configuration, the mixing volume is substantially fully retained within the second syringe barrel.

2. The coupling syringe system of claim 1, wherein the locking ring is configured to detachably connect to a discharge assembly.

3. The coupling syringe system of claim 2, wherein the discharge assembly comprises a needle cannula and a hub joined to a proximal end of the cannula, and wherein the male end portion at least partially fits into, and frictionally engages, the hub when the discharge assembly and the locking ring are detachably connected.

4. The coupling syringe system of claim 1, wherein the integral female end portion of the second syringe is detachably connected to the integral male end portion of the first syringe via engagement of the one or more exteriorly protruding members and one or more threads on an inward-oriented surface of the locking ring, which extend toward a syringe axis.

5. The coupling syringe system of claim 1, wherein the integral female end portion of the second syringe is detached from the integral male end portion of the first syringe.

6. The coupling syringe system as recited in claim 1, further comprising an outwardly projecting flange near the first syringe proximal end.

7. The coupling syringe system as recited in claim 1, further comprising an outwardly projecting flange near the second syringe proximal end.

8. The coupling syringe system as recited in claim 1, wherein the locking ring is rotatably coupled relative to the integral male end portion of the first syringe.

9. The coupling syringe system as recited in claim 1, wherein the locking ring surrounds the male end portion and is threadingly coupled with the one or more exteriorly protruding members, and wherein the one or more exteriorly protruding members are disposed on an outward-oriented surface of the opening wall, extending away from a syringe axis, of the female end portion.

10. The coupling syringe system as recited in claim 1, wherein the integral male end portion of the first syringe is disposed within the integral female end portion of the second syringe.

11. The coupling syringe system as recited in claim 1, wherein the locking ring is rotatably coupled with the integral male end portion of the first syringe and the locking ring is threadingly coupled with the one or more exteriorly protruding members of the second syringe.

12. The coupling syringe system as recited in claim 1, wherein the the first composition includes a drug delivery system.

13. The coupling syringe system as recited in claim 12, wherein the second composition includes a drug.

14. The coupling syringe system as recited in claim 13, wherein the drug includes lyophilized leuprolide acetate.

15. The coupling syringe system as recited in claim 12, wherein the drug delivery system includes Poly (D,L-lactide-co-glycolide) dissolved in a biocompatible solvent N-methyl 2-pyrrolidone.

16. The coupling syringe system as recited in claim 1, wherein the first syringe is directly coupled to the second syringe such that no independent coupling means is present therebetween.

17. The coupling syringe system as recited in claim 1, wherein the first syringe is configured for administration to a patient and wherein the first syringe is approximately the same size as the second syringe.

18. The coupling syringe system as recited in claim 1, wherein the first syringe including the first syringe tip with the integral male end portion is defined by a unitary body; and
   wherein the second syringe including the second syringe tip with the integral female end portion is defined by a unitary body.

19. A coupling syringe system for forming a mixed medical composition, the system comprising:
   a first single dose syringe including a first syringe barrel having a first syringe distal end, the first syringe barrel further including a first syringe tip with an integral male end portion having a single two-way fluid passage formed with an inner surface of the male end portion and a locking ring at the first syringe distal end, wherein the locking ring is spaced from an outer surface of the male end portion;
   a first syringe plunger slidably disposed within the first syringe barrel and configured to move to a position at the first syringe distal end, a first volume of a first composition is retained within the first syringe barrel including the first syringe tip;
   a second single dose syringe including a second syringe barrel having a second syringe distal end, the second syringe further including at the second syringe distal end a second syringe tip with an integral female end portion coupled with the second syringe barrel, wherein the female end portion comprises one or more exteriorly protruding members adapted to detachably fit the locking ring and an opening defined by an opening wall;
   a second syringe plunger slidably disposed within the second syringe barrel and configured to move to a position at the second syringe distal end, a second volume of a second composition is retained within the second syringe barrel; and
   wherein, when the first and second syringes are coupled, the male end portion is received by the opening of the female end portion at the first and second syringe distal ends, the single two-way fluid passage of the integral male end portion extends into the female end portion between the first and second syringe barrels, and the opening wall and the one or more exteriorly protruding members are received by the spacing between the locking ring and the outer surface of the male end portion, thereby allowing for a single, fluid tight attachment site configured for back and forth transfer and mixing of the first and second volumes through the single two-way fluid passage between the first syringe and the second syringe, wherein a mixing volume including the first and second volumes of the is substantially fully transitioned between the first and second syringes in corresponding first and second mixing configurations:
   in the first mixing configuration, the mixing volume is substantially fully retained within the first syringe barrel, and
   in the second mixing configuration, the mixing volume is substantially fully retained within the second syringe barrel.

20. The coupling syringe system as recited in claim 19, wherein the locking ring couples the first syringe to the second syringe and forms a fluid tight engagement configured for back and forth transfer of the drug delivery system and the drug between the syringes.

21. The coupling syringe system as recited in claim 19, wherein the drug includes lyophilized leuprolide acetate.

22. The coupling syringe system as recited in claim 19, wherein the drug delivery system includes Poly (D,L-lactide-co-glycolide) dissolved in a biocompatible solvent N-methyl 2-pyrrolidone.

23. The coupling syringe system as recited in claim 19, wherein, when the first and second syringes are coupled, movement of the first syringe plunger toward the second syringe effectuates delivery of one or both of the drug delivery system or the drug through the male end portion and directly into the second syringe barrel.

\* \* \* \* \*

UNITED STATES PATENT AND TRADEMARK OFFICE
CERTIFICATE OF CORRECTION

| | |
|---|---|
| PATENT NO. | : 8,226,598 B2 |
| APPLICATION NO. | : 10/634656 |
| DATED | : July 24, 2012 |
| INVENTOR(S) | : Dunn et al. |

It is certified that error appears in the above-identified patent and that said Letters Patent is hereby corrected as shown below:

In column 12, line 15, in Claim 19, after "volumes", delete "of the", therefor

Signed and Sealed this
Thirteenth Day of November, 2012

David J. Kappos
*Director of the United States Patent and Trademark Office*